United States Patent [19]

Kleine-Homann

[11] Patent Number: 4,788,343

[45] Date of Patent: Nov. 29, 1988

[54] PRODUCTION OF CYCLOHEPTANONE

[75] Inventor: Walter Kleine-Homann, Dülmen, Fed. Rep. of Germany

[73] Assignee: Hüls Aktiengesellschaft, Marl, Fed. Rep. of Germany

[21] Appl. No.: 85,186

[22] Filed: Aug. 14, 1987

[30] Foreign Application Priority Data

Nov. 6, 1986 [DE] Fed. Rep. of Germany ....... 3637787

[51] Int. Cl.⁴ ............................................. C07C 45/45
[52] U.S. Cl. .................................................. 568/355
[58] Field of Search ........................................ 568/355

[56] References Cited

U.S. PATENT DOCUMENTS

| | | | |
|---|---|---|---|
| 1,702,844 | 2/1929 | Ruzicka | 568/355 |
| 1,702,851 | 2/1929 | Ruzicka | 568/355 |
| 1,702,852 | 2/1929 | Ruzicka | 568/355 |
| 2,529,825 | 11/1950 | Stoll | 568/355 |
| 2,863,923 | 12/1958 | Bortnick | 568/355 |

Primary Examiner—James H. Reamer
Attorney, Agent, or Firm—Gilbert L. Wells

[57] ABSTRACT

Cycloheptanone (suberone) is prepared by first evaporating suberic-acid esters which are reacted in alcoholic and/or aqueous dilution in the gas phase on aluminum oxide support catalyst doped with zinc oxide and/or cerium oxide at temperatures between 300° and 600° C.

13 Claims, No Drawings

PRODUCTION OF CYCLOHEPTANONE

Applicant claims priority under 35 USC 119 for application No. P 36 37 787.2 filed Nov. 6, 1986 in the Patent Office of West Germany.

BACKGROUND OF THE INVENTION

The field of the invention is cyclic ketones and the present invention is particularly concerned with the production of cycloheptanone from suberic-acid.

The synthesis of cyclic ketones such as cycloheptanone (suberone) has been comprehensively described in the literature. The chemical structure, preparation and physical properties of suberic-acid and cycloheptanone are disclosed in the Kirk-Othmer, "Encyclopedia of Chemical Technology" 2nd Edition, Volumes 1, (1963) Pages 249–250 and 12, (1967) Page 106 respectively and the preparation of ketones is disclosed generally in Volume 12, (1967) at Pages 101–169, the disclosure of which is incorporated herein by reference.

As regards the so-called Dieckmann condensation of cycloheptanone, the reaction of a dicarboxylic acid ester is carried out in the presence of an alkali alcoholate. The maximum yield is about 75% when five- or six-link rings are formed. On the other hand, the use of dicarboxylic acid esters with longer chains (up to $C_{14}$) offers only slight yields when this method is employed (J. Org. Chem. 23, 1958, p. 1708).

Comparable yields also are obtained in the cyclization of adipic acid into cyclopentanone. The carbonates of zinc, of cadmium and of manganese are particularly suitable as catalysts. However, when subericacid is used, only a yield of about 40% of cycloheptanone is achieved (Izv. Akad. SSR, 1968, 3, pp. 632–636).

Similarly unsatisfactory values are achieved in the so-called Tiffenaeu-Demjanov ring-widening method. Butadiene and acrylonitrile are converted into 1-cyanocyclohexene-3 which is reduced into the amine and then is diazotized and converted into cycloheptanol. The cycloheptanone (suberone) is then available through dehydration of the cycloheptanol.

Substantially superior yields up to about 95% are achieved in the Ziegler condensation. However, this reaction requires equimolar quantities of alkylated alkali amides in solutions as dilute as possible (Ann. Chem. 504 (1933), pp. 95–130).

SUMMARY OF THE INVENTION

Having in mind the limitations of the prior art, it is an object of the present invention to provide a process whereby easily available raw materials produce cycloheptanone at high yields and selectivities and relatively few accessory materials alien to the system are used.

This object is achieved by a process for the preparation of cycloheptanone from suberic-acid esters, wherein suberic-acid esters are evaporated and are reacted in alcoholic and/or aqueous dilution in the gas phase on aluminum oxide support catalysts doped with zinc oxide and/or cerium oxide at temperatures between 300° and 600° C.

A suberic-acid ester is placed in an evaporator and heated to achieve a vapor state. The ester vapor is passed through a superheater and the alcohol or water is metered into the superheater so that the vapors mix before entry into a heated quartz tube containing the aluminum fixed bed catalyst. The ester and alcohol or water in the gas phase are passed over the fixed bed catalyst at temperatures between 300° and 600° C. and the reactor product is condensed. Cycloheptanone is separated in a distillation column from the reactor product. When water is used in the gas phase reaction, it is necessary to first separate the water before the cycloheptanone is separated by distillation.

DESCRIPTION OF THE PREFERRED EMBODIMENTS

This synthesis of cycloheptanone (suberone) from suberic-acid esters in the gas phase is new and unexpected at high yields and high selectivities using aluminum oxide support catalysts doped with zinc oxide and/or cerium oxide.

The preferred esters are the methyl-, ethyl-, propyl- and butyl-derivatives of suberic-acid or their mixtures. In view of their higher boiling points (greater than 340° C.), esters having alkyl groups with long chains (greater than $C_4$) are less suitable in practice. The initial substance can be a pure product or also the raw material directly obtained from the esterification is useful. Advantageously, the crude product contains an excess of the alcohol used in the esterification. Where appropriate, another alcohol, such as mentioned above, may be used in excess. Again, when the pure product is used, the addition of the above alcohols in excess increases the selectivity.

The alcohol may be metered both separately from the ester or mixed with the ester. The molar ratio of alcohol to ester preferably is 1–20:1, in particular, 3–15:1.

When the crude product from the esterification of suberic-acid is used, the process selectivity and its economy can be increased. No pressurizing apparatus is then needed to achieve shorter esterification times, even where dimethylester products are involved.

Where the crude product is used, a conversion between 90 and 95% is sought depending on the excess of alcohol in the esterification stage. The suberic-acid and the half-ester not converted are predominantly separated during evaporation and are returned to the esterification stage.

Aside the above-described dilutions using alcohol, water is also suitable as a diluent. To prevent ester saponification as much as possible, the water supplied should be fed-in separately. Preferably, the water is added after the suberic-acid esters have been evaporated. The molar ratio of water to ester preferably is 1–50:1, in particular, 3–20:1.

Another way to increase selectivity is to operate in an inert atmosphere, for instance, using nitrogen. The latter method however, incurs the drawback that by circumventing extreme cooling using partial-vapor application, there is some loss of the valuable end product.

Catalysts doped with zinc-oxide and/or cerium-oxide are suitable. Aluminum oxide is a suitable support material, for instance, commercial aluminum oxide, such as $Al_2O_3$ 3996 made by Harshaw Co. Preferably, the aluminum oxide support material is doped with 5 to 35 and especially with 8 to 20% by weight, of the cited metal oxides.

In order to carry out the reaction, first the suberic-acid ester is evaporated and reacted in the gas phase on the catalyst.

The reaction takes place at temperatures from about 300° to 600° C., and preferably between 400° and 500° C., in particular at normal pressure. Selectively, the reaction is carried out both at reduced and at excess pressure. Where long-chain alcohols are used, the reaction preferably is carried out at reduced pressure.

The reaction of the suberic-acid with the particular alcohol takes place with the use of conventional catalysts such as sulfuric acid, p-toluol sulfonic acid or butyl titanate. Commercial ion exchange resins, such as Lewatit SPC 108 and SPC 118, are also useful as catalysts. Where the pure ester is to be employed, the raw material is fractionated. When the crude ester product is employed as the initial substance and the esterification catalyst is an ion exchange resin, the ion exchange resin is first filtered off and next washed with an alcohol to prevent product losses.

The residue obtained following evaporation of the crude product and consisting predominantly of half-esters is useful again in the next esterification.

Preferably, the crude cycloheptanone (suberone) is processed by distillation. When water is also metered into the reactor, then the processing advantageously takes place in two stages. The two-phase mixture is first separated into an organic phase and aqueous phase. Taking into account the cycloheptanone (suberone) dissolved in the aqueous phase, the organic components of the water phase are separated by removing the water from the circuit to form a second organic phase.

The two organic phases are then combined and processed by distillation.

However, the separate processing of the water phase can also be circumvented by distilling the two-phase mixture. This single-stage processing by distillation incurs the drawback of a longer thermal load on the total output.

Conversions of 60 to 95% and selectivities of 50 to 80% are achieved in the reaction of the present invention.

Cycloheptanone (suberone) is employed in particular as a scent or as a pharmaceutical intermediate product.

SPECIFIC EXAMPLES

A. Esterification

Suberic-acid is placed with the alcohol in a ratio of 1:1 in a stirred flask on which is mounted a column and water remover. After the catalyst is added, the mixture is heated until reflux. When a water phase is formed, for instance when using butanol, the water is separated to shorten the reaction time. Upon reaching the desired conversion rate and when an ion exchanger is used as catalyst, this ion exchanger then is first separated and then washed with alcohol. Thereupon the filtrate is neutralized with sodium hydroxide just as in the illustrative case where p-toluol sulfonic acid is used as the catalyst.

Liquid residues collecting in the reactor during the evaporation of the crude product are used directly for the esterification procedure.

B. Reaction Into Cycloheptanone (Suberone)

1 liter of the particular catalyst is placed into an electrically heated quartz tube 1m long and 50 mm in diameter. Nitrogen flows through the reactor during the heating stage until the desired temperature of reaction has been reached. The temperature is sensed by a resistance thermometer mounted in a centered quartz tube 6 mm in diameter wherein it can be axially displaced into the desired position as needed.

The liquid input products are raised to the required temperature of reaction by an evaporator with a subsequent superheater and then are made to pass over the catalytic bed. The alcohol or water is supplied past the evaporator but before the superheater.

C. The Processing Of The Crude Output

The processing of the crude output of the suberone production is by means of distillation in a 0.5 m column fitted with fabric packing.

If an aqueous phase is formed in the crude product, it is separated and then processed separately using a water remover. The organic phase then being collected is combined with that of the reactor output and processed jointly. The purity of the desired cycloheptanone (suberone) as the main run is 99%.

If the aqueous phase is not treated separately but instead is directly removed from the two-phase reactor output, then partial back-cleaving of the unconverted ester portion takes place depending on the conditions of distillation.

EXAMPLES 1 THROUGH 10

Illustrative values obtained when metering the corresponding alcohol are listed in the table below:

| Example | Catalyst | Suberic-acid ester | Molar ratio alcohol/ester | Reaction temp. (C.°) | Conversion (%) | Selectivity (%) |
|---|---|---|---|---|---|---|
| 1 | A | I | 15 | 420 | 59 | 63 |
| 2 | C | II | 10 | 440 | 62 | 59 |
| 3 | A | III | 6 | 420 | 75 | 49 |
| 4 | C | IV | 5 | 450 | 72 | 66 |

The table below illustrates the values obtained when metering water:

| Example | Catalyst | Suberic-acid ester | Molar ratio water/ester | Reaction temp. (C.°) | Conversion (%) | Selectivity (%) |
|---|---|---|---|---|---|---|
| 5 | A | I | 20 | 440 | 65 | 76 |
| 6 | B | I | 3 | 460 | 82 | 61 |
| 7 | C | I | 10 | 480 | 85 | 56 |
| 8 | D | I | 10 | 420 | 62 | 72 |
| 9 | A | IV | 6 | 450 | 82 | 72 |
| 10 | E | I | 20 | 460 | 83 | 65 |

COMPARISON EXAMPLE

Suberic-acid methylester is reacted undiluted at 420° C. on catalyst A into cycloheptanone (suberone). Following distillation of the crude output, a main run with a purity of 99.2% is isolated. A selectivity of 38% is achieved at a conversion of 74%.

| Abbreviations: | |
|---|---|
| ester I | suberic-acid dimethylester |
| ester II | suberic-acid diethylester |
| ester III | suberic-acid diisopropylester |
| ester IV | suberic-acid dibutylester |
| catalyst A | 12% ZnO on $Al_2O_3$ |
| catalyst B | 18% ZnO on $Al_2O_3$ |
| catalyst C | 8% CeO on $Al_2O_3$ |
| catalyst D | 14% CeO on $Al_2O_3$ |
| catalyst E | 9% ZnO/7% CeO on $Al_2O_3$. |

I claim:

1. A process for the preparation of cycloheptanone from a suberic-acid ester, comprising evaporating a suberic-acid ester and reacting said ester in the gas phase on aluminum oxide support catalysts doped with a catalytic amount of an oxide selected from the group consisting of zinc oxide, cerium oxide or a mixture thereof at temperatures between 300° and 600° C. and diluting said evaporated ester with a compound selected from the group consisting of alcohol, water or a mixture thereof.

2. The process of claim 1, wherein said suberic-acid ester is selected from the group consisting of methylester of suberic-acid, ethylester of suberic-acid, propylester of suberic-acid, butylester of suberic-acid and mixtures thereof.

3. The process of claim 2, wherein said compound is an alcohol and a molar ratio of alcohol to ester of between 1 and 20:1, is used.

4. The process of claim 3, wherein said molar ratio is between 3 and 15:1.

5. The process of claim 3, wherein said alcohol has one to four carbon atoms.

6. The process of claim 2, wherein said compound is water and a molar ratio of water to ester of between 1 and 50 is used.

7. The process of claim 6, wherein said molar ratio is between 3 and 20.

8. The process of claim 6, wherein said water is added after the subericacid ester has been evaporated.

9. The process of claim 1, wherein said reaction is carried out at temperatures between 400° and 500° C.

10. The process of claim 1, wherein said reaction is carried out in the presence of said aluminum oxide support catalysts containing from 5 to 35 of said oxide.

11. The process of claim 10, wherein said aluminum oxide support catalysts contain 8 to 20% of said oxide.

12. The process of claim 1, wherein said reaction is carried out in an inert gas atmosphere.

13. The process of claim 1, wherein said alcohol is selected from the group consisting of methyl alcohol, ethyl alcohol, propoyl alcohol, butyl alcohol and mixtures thereof.

* * * * *